United States Patent
Petropavlova et al.

(10) Patent No.: US 8,603,456 B2
(45) Date of Patent: Dec. 10, 2013

(54) METHOD OF TREATING HAIR LOSS WITH COMPOSITIONS CONTAINING INTERLEUKIN-1

(75) Inventors: Ekaterina Viktorovna Petropavlova, Kusnacht (CH); Tatiana Vyacheslavovna Popkova, Moscow (RU)

(73) Assignee: United Technologies UT AG, Zurich (CH)

( * ) Notice: Subject to any disclaimer, the term of this patent is extended or adjusted under 35 U.S.C. 154(b) by 17 days.

(21) Appl. No.: 13/500,358

(22) PCT Filed: Oct. 8, 2009

(86) PCT No.: PCT/EP2009/063078
§ 371 (c)(1),
(2), (4) Date: Apr. 5, 2012

(87) PCT Pub. No.: WO2011/042056
PCT Pub. Date: Apr. 14, 2011

(65) Prior Publication Data
US 2012/0195853 A1    Aug. 2, 2012

(51) Int. Cl.
*A61K 38/20*    (2006.01)

(52) U.S. Cl.
USPC .................... 424/85.2; 530/351; 514/1.1

(58) Field of Classification Search
None
See application file for complete search history.

(56) References Cited

U.S. PATENT DOCUMENTS

| | | | |
|---|---|---|---|
| 5,120,534 A | 6/1992 | Hirai et al. | |
| 5,725,851 A * | 3/1998 | Wong et al. | 424/85.2 |
| 5,939,457 A * | 8/1999 | Miser | 514/557 |
| 6,268,180 B1 | 7/2001 | Gubler et al. | |

FOREIGN PATENT DOCUMENTS

| WO | WO89/05653 | * | 6/1989 |
| WO | PCT/EP2008/054574 | | 4/2008 |

* cited by examiner

*Primary Examiner* — Robert Landsman
*Assistant Examiner* — Bruce D Hissong
(74) *Attorney, Agent, or Firm* — Notaro, Michalos & Zaccaria P.C.

(57) ABSTRACT

Cosmetic methods for treating skin and/or hair, including steps of (a) applying to skin and/or hair a cosmetic composition comprising interleukin-1 for 3 to 70 days, followed by (b) withdrawing application of the composition for 14 to 70 days, and (c) repeating steps (a)-(b) at least once.

4 Claims, No Drawings

SEQUENCE LISTING

```
<160> NUMBER OF SEQ ID NOS: 1

<210> SEQ ID NO 1
<211> LENGTH: 159
<212> TYPE: PRT
<213> ORGANISM: Homo sapiens
```

```
<400> SEQUENCE: 1

Ser Ala Pro Phe Ser Phe Leu Ser Asn Val Lys Tyr Asn Phe Met Arg
1               5                   10                  15

Ile Ile Lys Tyr Glu Phe Ile Leu Asn Asp Ala Leu Asn Gln Ser Ile
            20                  25                  30

Ile Arg Ala Asn Asp Gln Tyr Leu Thr Ala Ala Ala Leu His Asn Leu
        35                  40                  45

Asp Glu Ala Val Lys Phe Asp Met Gly Ala Tyr Lys Ser Ser Lys Asp
    50                  55                  60

Asp Ala Lys Ile Thr Val Ile Leu Arg Ile Ser Lys Thr Gln Leu Tyr
65                  70                  75                  80

Val Thr Ala Gln Asp Glu Asp Gln Pro Val Leu Leu Lys Glu Met Pro
            85                  90                  95

Glu Ile Pro Lys Thr Ile Thr Gly Ser Glu Thr Asn Leu Leu Phe Phe
            100                 105                 110

Trp Glu Thr His Gly Thr Lys Asn Tyr Phe Thr Ser Val Ala His Pro
            115                 120                 125

Asn Leu Phe Ile Ala Thr Lys Gln Asp Tyr Trp Val Cys Leu Ala Gly
        130                 135                 140

Gly Pro Pro Ser Ile Thr Asp Phe Gln Ile Leu Glu Asn Gln Ala
145                 150                 155
```

METHOD OF TREATING HAIR LOSS WITH COMPOSITIONS CONTAINING INTERLEUKIN-1

FIELD OF THE INVENTION

The invention relates to cosmetic methods for treating the skin and/or hair with cosmetic compositions containing interleukin-1, more specifically the human recombinant interleukin-1 alpha.

BACKGROUND OF THE INVENTION

Interleukin-1 family of cytokines is represented by some members. Among them, interleukin-1 alpha and interleukin-1 beta are two major isoforms with amino acid sequences well-known from the art. Among them, only interleukin-1 alpha is produced in substantial amounts in normal human epidermis, about 50:50 in living epidermal cells and stratum corneum. Gahring L C, Buckley A, Daynes R A. Presence of epidermal-derived thymocyte activating factor/interleukin 1 in normal human stratum corneum. *J. Clin. Invest.* 1985 76(4):1585-91. Hauser C, Saurat J H, Schmitt A, Jaunin F, Dayer J M. Interleukin 1 is present in normal human epidermis. *J. Immunol.* 1986, 136(9):3317-23. Schmitt A, Hauser C, Jaunin F, Dayer J M, Saurat J H. Normal epidermis contains high amounts of natural tissue IL 1 biochemical analysis by HPLC identifies a MW approximately 17 Kd form with a pH 5.7 and a MW approximately 30 Kd form. *Lymphokine Res.* 1986, 5(2):105-18. It is well-documented that IL-1 alpha is a primary inductor of epidermis renewal through a double paracrine regulatory mechanism, including expression and release a set of growth factors, e.g. KGF, HGF, and GM-CSF, critical for keratinocyte proliferation and differentiation. Werner S, and Smola H. Paracrine regulation of keratinocyte proliferation and differentiation. *Trends Cell. Biol.* 2001, 11(4):143-146. Interleukin-1 alpha orchestrates collagen turnover in dermis through complex regulation of both collagen synthesis and degradation pathways. Postlethwaite A E, Raghow R, Stricklin G P, Poppleton H, Seyer J M, Kang A H. Modulation of fibroblast functions by interleukin 1: increased steady-state accumulation of type I procollagen messenger RNAs and stimulation of other functions but not chemotaxis by human recombinant interleukin 1 alpha and beta. *J. Cell. Biol.* 1988, 106(2):311-8. Duncan M R, Berman B. Differential regulation of collagen, glycosaminoglycan, fibronectin, and collagenase activity production in cultured human adult dermal fibroblasts by interleukin 1-alpha and beta and tumor necrosis factor-alpha and beta. *J. Invest. Dermatol.* 1989, 92(5):699-706. Interleukin-1 alpha stimulates dermal fibroblasts to produce glycosaminoglycans, e.g. hyaluronic acid. Postlethwaite A E, Smith G N Jr, Lachman L B, Endres R O, Poppleton H M, Hasty K A, Seyer J M, Kang A H. Stimulation of glycosaminoglycan synthesis in cultured human dermal fibroblasts by interleukin 1. Induction of hyaluronic acid synthesis by natural and recombinant interleukin 1s and synthetic interleukin 1 beta peptide 163-171. *J. Clin. Invest.* 1989, 83(2):629-36. Interleukin-1 alpha plays a role in keeping skin barrier function in a good condition. Ye J, Garg A, Calhoun C, Feingold K R, Elias P M, Ghadially R: Alterations in cytokine regulation in aged epidermis: Implications for permeability barrier homeostasis and inflammation. I. IL-1 gene family. *Exp. Dermatol.* 11:209-216, 2002. Interleukin-1 alpha is a modifier of activity of dermal papilla cells. Boivin W A, Jiang H, Utting O B, Hunt D W. Influence of interleukin-1alpha on androgen receptor expression and cytokine secretion by cultured human dermal papilla cells. *Exp Dermatol.* 2006, 15(10):784-93. Thus, interleukin-1 alpha is the epidermal cytokine that regulates skin functions and may be used as cosmetic benefit agent, for example, to keep skin in a good condition and stimulate production of collagen and hyaluronic acid in dermis.

PCT/EP2008/054574 discloses cosmetic compositions comprising interleukin-1 alpha. However, the growing evidence suggests that cosmetic efficacy of these compositions dramatically decrease under continuous use. Thus, there is the need in cosmetic methods or regimens of optimal use of cosmetic compositions comprising interleukin-1 to achieve optimal cosmetic benefit for subjects in need thereof.

Interleukin-1 may be prepared in industrial scale and suitable purity as recombinant polypeptides identical to the native ones. Gubler U., et al., Recombinant human interleukin 1 alpha: purification and biological characterization. *J. Immunol.* 1986, 136:2492-2497. U.S. Pat. No. 6,268,180 discloses a method of preparation of human recombinant interleukin-1 alpha.

It is an object of the present invention to provide a cosmetic method for treating the skin and/or hair, the method comprising the steps of applying to the skin and/or hair a cosmetic composition comprising an interleukin-1 in a cosmetically acceptable vehicle for a period of 3 to 70 days followed by withdrawing the application of the cosmetic composition for a period of 14 to 70 days and repeating abovementioned steps at least once.

DETAILED DESCRIPTION OF THE INVENTION

The present invention provides a cosmetic method for treating the skin and/or hair, the method comprising the steps of: (a) applying to the skin and/or hair a cosmetic composition comprising an interleukin-1 in a cosmetically acceptable vehicle for a period of 3 to 70 days followed by; (b) withdrawing the application of the cosmetic composition for a period of 14 to 70 days; and (c) repeating steps (a)-(b) at least once.

In preferred embodiments of the present invention, the interleukin-1 is a human recombinant interleukin-1.

As used herein, the term "human recombinant interleukin-1" refers to interleukin-1, which is expressed using suitable recombinant protein expression systems that use, for example, *E-coli* or yeast as the host. Preparation of human recombinant interleukin-1 is described, for example, in *J. Immunol.* 1986, 136(7):2429 and in U.S. Pat. No. 6,268,180.

In preferred embodiments of the present invention, the human recombinant interleukin-1 is a human recombinant interleukin-1 alpha or a human recombinant interleukin-1 beta.

In more preferred embodiments of the present invention, the human recombinant interleukin-1 is a human recombinant interleukin-1 alpha.

As used herein, the term "the human interleukin-1 alpha" refers to the polypeptide well-known from the art, published, for example, in UniProt database No. P01583, and having the following amino acid sequence:

As used herein, the term "the human interleukin-1 alpha" refers to the polypeptide well-known from the art, published, for example, in UniProt database No. P01583, (http://www.uniprot.org/uniprot/P01583), and having the following amino acid sequence SEQ ID NO: 1:
Ser-Ala-Pro-Phe-Ser-Phe-Leu-Ser-Asn-Val-Lys-Tyr-Asn-Phe-Met-Arg-Ile-Ile- Lys-Tyr-Glu-Phe-Ile-Leu-Asn-Asp-Ala-Leu-Asn-Gln-Ser-Ile-Ile-Arg-Ala-Asn- Asp-Gln-Tyr-Leu-Thr-Ala-Ala-Ala-Leu-His-Asn-Leu-Asp-Glu-Ala-Val-Lys-Phe- Asp-Met-Gly-Ala-Tyr-Lys-Ser-Ser-Lys-Asp-Asp-Ala-Lys-Ile-Thr-Val-Ile-Leu- Arg-Ile-Ser-Lys-Thr-Gln-Leu-Tyr-Val-Thr-Ala-Gln-Asp-Glu-Asp-Gln-Pro-Val- Leu-Leu-Lys-Glu-Met-Pro-Glu-Ile-Pro-Lys-Thr-Ile-Thr-Gly-Ser-Glu-Thr-Asn- Leu-Leu-Phe-Phe-Trp-Glu-Thr-His-Gly-Thr-Lys-Asn-Tyr-Phe-Thr-Ser-Val-Ala- His-Pro-Asn-Leu-Phe-Ile-Ala-Thr-Lys-Gln-Asp-Tyr-Trp-Val-Cys-Leu-Ala-Gly- Gly-Pro-Pro-Ser-Ile-Thr-Asp-Phe-Gln-Ile-Leu-Glu-Asn-Gln-Ala As used herein, the term "analogue of human interleukin-1 alpha" refers to an interleukin-1 alpha that contains one or more amino acid substitutions, deletions, additions, or rearrangements compared with human interleukin-1 alpha at sites such that the interleukin-1 alpha analogue still retains the in vitro and/or in vivo biological activity of the human interleukin-1 alpha. Examples of such analogues are described in U.S. Pat. No. 6,268,180 and U.S. Pat. No. 5,120,534.

As used herein, the term "derivative of human interleukin-1 alpha" refers to human interleukin-1 alpha and the human interleukin-1 alpha analogues that are chemically or enzymatically derivatized at one or more constituent amino acids, including side chain modifications, backbone modifications, and N-and C-terminal modifications, by for example acetylation, acylation, hydroxylation, methylation, amidation, phosphorylation, pegylation, or glycosylation, and that retain the in vivo biological activity of interleukin-1 alpha. An example of a human interleukin-1 alpha derivative is N6-myristoyl-Lys11-interleukin-1 alpha and HisTag-interleukin-1 alpha.

In preferred embodiments of the present invention, the content of the human recombinant interleukin-1 in compositions of the present invention is from $10^{-7}$ to $10^{-4}$ wt. %.

As used herein, the term "cosmetic composition" refers to any composition suitable for topical application to the skin and/or hair of a human subject for enhancing the health, hygiene or appearance of the subject. In this respect, the term "skin" encompasses whole skin or any portion of the skin, including skin appendages like hair and nails.

As used herein, the term "cosmetically acceptable vehicle" refers to one or more safe liquid, semi-solid, solid diluents, or encapsulating substances which are compatible with interleukin-1, and are suitable for administration to any portion of the human skin, hair, and nail without undue/unacceptable aesthetic effects, e.g., greasiness, color, odor, etc. Non-exclusive examples of such cosmetically acceptable vehicles include distilled or deionized water, propyleneglycol, glycerol, and oil. The term "compatible", as used herein, means the substance capable of being mixed with the interleukin-1 without interaction in a manner which would substantially reduce the interleukin-1's stability and/or efficacy.

The compositions of the present invention can comprise optional ingredients. Such optional ingredients generally are used individually at levels from about 0.0005% to about 10.0%, preferably from about 0.005% to about 1.0% by weight of the composition.

Examples of suitable optional ingredients include, but are not limited to, buffers, depigmentation agents; reflectants; humectants; antimicrobial (e.g., antibacterial) agents; UV absorbers; anti-acne agents; anti-aging agents; anti-wrinkling agents, antiseptics; local anesthetics; wound healing promoters; deodorants and antiperspirants; skin emollients and skin moisturizers; tanning agents; skin lightening agents; antifungals; depilating agents; external analgesics; counterirritants; anti-diaper rash agents; make-up preparations; vitamins and nutrients such as thiamin, riboflavin, niacin, pantothenates, pyridoxine, folic acid, cobalamin, biotin, choline, inositol, ascorbic acid, lipoic acid, carnitine, and etc.; amino acids and their derivatives such as alanine, arginine, asparagine, aspartic acid, carnitine, citrulline, cysteine, dimethylglycine, gamma-aminobutyric acid, glutamic acid, glutamine, glutathione, glycine, histidine, isoleucine, leucine, lysine, methionine, ornithine, phenylalanine, praline, serine, taurine, threonine, tryptophan, tyrosine, valine; minerals such as boron, calcium, chromium, cobalt, copper, fluoride, germanium, iodine, iron, lithium, magnesium, manganese, molybdenum, phosphorus, potassium, selenium, silicon, sodium, sulfur, vanadium, zinc; herbal extracts; retinoids; bioflavonoids; anti-oxidants; skin conditioners; hair lighteners; chelating agents; cell turnover enhancers; coloring agents; sunscreens and the like, and mixtures thereof.

Examples of suitable buffers include, but are not limited to, buffers at a concentration effective to maintain the pH of the composition at between about 4.0 to about 10.0 such as phosphate buffer, acetate, citrate buffer, succinate buffer, and glycine buffer.

Examples of suitable reflectants include, but not limited to, mica, alumina, calcium silicate, glycol dioleate, glycol distearate, silica, sodium magnesium fluorosilicate, and mixtures thereof.

Examples of suitable UV absorbers include, but not limited to, benzophenone, bomelone, butyl paba, cinnamidopropyl trimethyl ammonium chloride, disodium distyrylbiphenyl disulfonate, paba, potassium methoxycinnamate, and mixtures thereof.

Examples of suitable humectants include, but not limited to, water soluble liquid polyols selected from the group comprising glycerine, propylene glycol, hexylene glycol, butylene glycol, pentylene glycol, dipropylene glycol, and mixtures thereof. The humectant is preferably present in an amount of from about 0 percent to about percent, more preferably from about 0.5 percent to about 5 percent, based on the overall weight of the composition.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl kertain amino acids; capryloyl pea amino acids;

cocodimonium hydroxypropyl silk amino acids; corn gluten amino acids; cysteine; glutamic acid; glycine; hair keratin amino acids; hair amino acids such as aspartic acid, threonine, serine, glutamic acid, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Examples of suitable proteins include, but not limited to, collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultra-high-sulfur proteins, intermediate filament-associated proteins, high-tyrosine proteins, high-glycine tyrosine proteins, tricohyalin, arginine-rich peptides like as oligoarginines $(Arg)_8$, and mixtures thereof.

Examples of suitable antiperspirants and deodorants include, but not limited to, aluminium chlorohydrates, aluminium zirconium chlorohydrates, and mixtures thereof.

Examples of sunscreen agents include, but not limited to, titanium dioxide and zinc oxide.

Examples of suitable counterirritants include, but not limited to, camphor, menthol, methyl salicylate, peppermint and clove oils, ichtammol, and mixtures thereof.

Examples of suitable anti-aging agents include, but are not limited to, inorganic sunscreens such as zinc oxide; organic sunscreens such as octyl-methyl cinnamates and derivatives thereof; retinoids; vitamins such as vitamin C, vitamin B, and derivatives thereof; antioxidants including acid such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucopehtonic acid, glucoheptono 1,4-lactone, gluconic acid, gluconolactone, glucuronic acid, glucurronolactone, glycolic acid, isopropyl pyruvate, methyl pyruvate, mucic acid, pyruvia acid, saccharic acid, saccaric acid 1,4-lactone, tartaric acid, and tartronic acid; succinic acid or salts thereof; acids such as beta-hydroxybutyric acid, beta-phenyllactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, safflower, and mixtures thereof. Suitable amounts of anti-aging agents include, based upon the total weight of the composition, from about 0.01 percent to about 10 percent, and preferably from about 0.04 percent to about 5 percent.

Examples of suitable depigmentation agents include, but are not limited to, hydroquinone and it derivatives; vitamins such as niacin, vitamin C and its derivatives; extracts such as chamomile and green tea, and mixtures thereof.

Examples of skin lightening agents include, but not limited to, hydroquinone, catechol and its derivatives, ascorbic acid and its derivatives, and mixtures thereof.

The compositions of the invention are prepared by standard techniques well known to those skilled in the art. Such procedures include, but are not limited to, mixing the interleukin-1 with other ingredients of the composition in conventional manner. Guidance for the preparation of cosmetic or dermatological compositions of the invention can be found in "Remington: The science and practice of pharmacy" 20th ed. Mack Publishing, Easton Pa., 2000 ISBN 0-912734-04-3 and "Encyclopaedia of Pharmaceutical Technology", edited by Swarbrick, J. & J. C. Boylan, Marcel Dekker, Inc., New York, 1988 ISBN 0-8247-2800-9 or a newer edition. As well known to the skilled person, illustrative additives to dermatological compositions include, but is not limited to: ointment bases, solvents, buffering agents, pH-adjusting agents, preservatives, humectants, chelating agents, antioxidants, stabilizers, emulsifying agents, suspending agents, gel-forming agents, perfumes, and skin protective agents.

The compositions of the present invention can be formulated in a variety of forms including, but are not limited to, lotions, serums, gels, emulsions, creams, sprays, and solutions.

In preferred embodiments of the present invention, the compositions are useful for regulating the skin condition, visible and/or tactile discontinuities in skin (especially the skin surface; such discontinuities are generally undesirable). Such discontinuities may be induced or caused by internal and/or external factors, and include the signs of skin aging described herein. The term "regulating skin condition" includes prophylactically regulating and/or therapeutically regulating skin condition, including visible and/or tactile discontinuities in skin. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, discontinuities in skin. Regulating skin condition involves improving skin appearance and/or feel.

The compositions of the present invention are particularly advantageous for regulating signs of skin aging, more especially visible and/or tactile discontinuities in skin texture associated with aging. "Regulating the signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). As used herein, prophylactically regulating such signs includes delaying, minimizing and/or preventing signs of skin aging. As used herein, therapeutically regulating such signs includes ameliorating, e.g., diminishing, minimizing and/or effacing signs of skin aging.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The compositions of the present invention are particularly advantageous for regulating signs of cellulite-affected skin, more especially visible and/or tactile discontinuities in skin texture associated with local fat depositions and irregularity of dermis-hypodermis border associated with such local fat depositions.

The compositions of the present invention are particularly advantageous for keeping skin appendages in a good condition preferably providing such benefits as: the prevention and treatment of hair loss, regeneration of damaged hair and stimulating hair growth in subjects in need thereof, improvement of nail health and appearance, acceleration of nail growth and regeneration, elimination nail problems such as changes in the shape and texture of nails, thickened nails, nail fragility, and brittle nails.

In preferred embodiments of the present invention, at the step of applying a cosmetic composition of the present invention, an effective amount of the composition is topically applied to the skin and/or hair, and is preferably left on the skin for a period of at least about 15 minutes, more preferably at least about 30 minutes, even more preferably at least about 1 hour, most preferably for at least several hours, e.g., up to about 12 hours. This method can be reapplied from 1 to about 5, preferably from 1 to 3 times per day. Typically, the effective amount of the composition is from about 1 gram to about 100 grams, preferably from about 1 gram to about 20 grams.

In preferred embodiments of the present invention, at the step of withdrawing the application of the cosmetic composition, any cosmetic composition comprising interleukin-1 should not been applied to the skin and/or hair.

In preferred embodiments of the present invention, at the step of withdrawing the application of the cosmetic composition, no cosmetic composition may be applied to the skin and/or hair of a subject.

In preferred embodiments of the present invention, at the step of withdrawing the application of the cosmetic composition, placebo and/or any cosmetic composition which does not comprises interleukin-1 may be topically applied to the skin and/or hair of a subject in amounts and daily regimen, which are known to skilled in the art.

The following examples are presented to demonstrate the invention. The examples are illustrative only and are not intended to limit the scope of the invention in any way.

Example 1

This example demonstrates that cosmetic efficacy of compositions comprising interleukin-1 decreases under continuous use.
1) Anti-cellulite study. The study was a randomized, double-blinded, placebo-controlled trial. The composition containing 0.00001 wt. % of human recombinant interleukin-1 alpha in tris-buffered water-oil emulsion (Test Article) or placebo were applied twice-a-day for ten weeks to the cellulite-affected skin region of thighs of twenty women with average age 43.5±8.8. Thighs were randomly assigned to the Test Article or Placebo groups. If the left thigh of a volunteer was assigned to receive topical application of the Test Article, then the right thigh of the volunteer was assigned to receive topical application of Placebo. If the left thigh of a volunteer was assigned to receive topical application of Placebo, then the right thigh of the volunteer was assigned to receive topical application of the Test Article. The final distribution was as follows: 20 thighs in the Test Article group (hereafter the Test group) and 20 thighs in the Placebo group (hereafter the Placebo group). Cosmetic efficacy of the treatment was assessed by evolution of hypodermis-dermis junction distance (JD) as a measure of a cellulite severity. Significant statistical differences in the JD evolution were observed between the Test and the Placebo group (p<0.05). There were statistically significant differences in the Test group between JD mean values at baseline level (day 0) and those at days 28 (−21.5%, p=0.0001), 56 (−17.7%, p=0.0001), and 70 (−21.1%, p=0.0001). Decrease in JD means the improvement of regularity of hypodermis-dermis junction border and cellulite severity, the primary endpoint in the cellulite treatment. However, the cosmetic efficacy of the composition decreases with time (Table 1).

TABLE 1

Junction Distance evolution rates

| Treatment Period, days | JD evolution rate, % per day |
|---|---|
| 0-28 | −0.77% |
| 28-56 | +0.14% |

Table 1 shows that the rate of improvement of regularity of hypodermis-dermis JD, the measure of cosmetic efficacy of the composition, decreases under continuous use of the composition from −0.77% per day at first month of the treatment to +0.14% per day at the second one.
2) Anti-aging study. The study was a randomized, double-blinded, placebo-controlled trial. The composition containing 0.00001 wt. % of human recombinant interleukin-1 alpha in tris-buffered water-oil emulsion (Test Article) or Placebo were applied twice-a-day for eight weeks to the skin region of forearms of twenty women with average age about 55 years. Cosmetic efficacy of the treatment was assessed by evolution of Number of Dark Pixels (NDP) on ultrasonograms of the treated areas. The NDP on skin ultrasonograms corresponds to low echogenic areas, e.g. fat and water depositions in the dermal fibrous protein network. Decrease in NDP during the treatment corresponds to the improvement of collagen-elastin network in skin dermis. Significant differences in NDP evolution rates were observed at days 14, 28, 56, and 70 between the Test group and the Placebo group (p<0.05). There were statistically significant differences in NDP in the Test group between mean values at baseline level (day 0) and those at days 28 (p=0.03), and 56 (p=0.006). However, the cosmetic efficacy of the composition decreases with time (Table 2).

TABLE 2

NDP evolution rates

| Treatment Period, days | NDP evolution, % per day |
|---|---|
| 0-28 | −1.92% |
| 28-56 | +0.21% |

Table 2 shows that the rate of improvement of collagen-elastin network in dermis of aging skin, the measure of cosmetic efficacy of the composition, decreases under continuous use of the composition from −1.92% per day at first month of the treatment to +0.21% per day at the second one.
Thus, cosmetic efficacy of compositions containing interleukin-1 decreases under continuous use.

Example 2

This example demonstrates the cosmetic method of the present invention. Six female subjects with hair loss rate from about 150 to about 200 hair per day applied to the scalp a cosmetic composition containing 0.000005 wt. % of human recombinant interleukin-1 alpha in tris-buffered water-oil emulsion continuously once-a-day for 33 days (Control, n=3) or applied the same composition by the cosmetic method (Test, n=3) comprising the steps of (a) applying to the scalp the cosmetic composition for 3 days followed by (b) withdrawing the application of the cosmetic composition for a period of 14 days; and (c) repeating steps (a)-(b) once. Results are presented in Table 3 as evolution in hair loss rate in percent of basal.

TABLE 3

Evolution of Hair loss rate

| | Hair loss per day, % of basal (day 0) | |
|---|---|---|
| Day | Control | Test |
| 17 | −21 | −49 |
| 34 | −11 | −73 |

Table 3 shows that the cosmetic method of the present invention is much effective in decreasing excessive hair loss rate as compared to the continuous mode of use the composition of the present invention. The cosmetic effect achieved in subjects treated in accordance with the treatment regimen of the cosmetic method of the present invention is greater than the effect achievable with the same composition under continuous use for the same treatment period and under otherwise equal conditions.

Example 3

This example demonstrates the cosmetic method of the present invention. Eight females applied to the cellulite-affected skin region of thighs a cosmetic composition containing 0.000005 wt. % of human recombinant interleukin-1 alpha in tris-buffered water-oil emulsion continuously (once-a-day for 154 days, Control, n=4) or applied the same composition by the cosmetic method (Test, n=4) comprising the steps of (a) applying to the skin the cosmetic composition for 70 days followed by (b) withdrawing the application of the cosmetic composition for a period of 28 days; and (c) repeating applying to the skin the cosmetic composition for 28 days followed by (b) withdrawing the application of the cosmetic composition for a period of 28 days. Results are presented in Table 4 as evolution in Junction Distance in time.

TABLE 4

Evolution of Junction Distance (JD) in time

| | JD evolution, % of basal (day 0) | |
|---|---|---|
| Day | Control | Test |
| 154 | −23 | 42 |

Table 4 shows that the cosmetic method of the present invention is much effective in the improvement of regularity of hypodermis-dermis junction under cellulite as compared to the continuous mode of use the composition of the present invention. The cosmetic effect achieved in subjects treated in accordance with the treatment regimen of the cosmetic method of the present invention is greater than the effect achievable with the same composition under continuous use for the same treatment period and under otherwise equal conditions.

Example 4

This example demonstrates the cosmetic method of the present invention. Six females applied to the face skin a cosmetic composition containing 0.000005 wt. % of human recombinant interleukin-1 alpha in tris-buffered water-oil emulsion continuously (once-a-day for 168 days, Control, n=3) or applied the same composition by the cosmetic method (Test, n=3) comprising the steps of (a) applying to the skin the cosmetic composition for 28 days followed by (b) withdrawing the application of the cosmetic composition for a period of 28 days; and (c) applying to the skin the cosmetic composition for 28 days followed by withdrawing the application of the cosmetic composition for a period of 70 days. Results are presented in Table 5 as evolution in skin firmness assessed as evolution of surface of area within the max and min envelope curves at a cutometer plot (F3). The decrease in F3 corresponds to improvement of skin firmness.

TABLE 5

Evolution of skin firmness in time

| | Skin firmness evolution, % of basal F3 (day 0) | |
|---|---|---|
| Day | Control | Test |
| 168 | −17 | −32 |

Table 5 shows that the cosmetic method of the present invention is much effective in the improvement of skin firmness as compared to the continuous mode of use the composition of the present invention. The cosmetic effect achieved in subjects treated in accordance with the treatment regimen of the cosmetic method of the present invention is greater than the effect achievable with the same composition under continuous use for the same treatment period and under otherwise equal conditions.

The invention claimed is:

1. A method for treating hair loss, comprising the steps of:
   (a) applying to the hair a composition comprising an interleukin-1 in an acceptable vehicle for a period of 3 to 70 days;
   (b) withdrawing the application of the composition for a period of 14 to 70 days; and
   (c) repeating steps (a)-(b) at least once.

2. The method of claim 1, wherein the interleukin-1 is a human recombinant interleukin-1.

3. The method of claim 2, wherein the content of the human recombinant interleukin-1 in the composition is from $10^{-7}$ to $10^{-4}$ wt. %.

4. The method of claim 2, wherein the human recombinant interleukin-1 is a human recombinant interleukin-1 alpha.

* * * * *